(12) United States Patent
Hu et al.

(10) Patent No.: US 11,730,408 B2
(45) Date of Patent: Aug. 22, 2023

(54) SYSTEMS AND METHODS FOR HUMAN-MACHINE PARTNERED PTSD PREDICTION

(71) Applicant: The MITRE Coporation, McLean, VA (US)

(72) Inventors: Qian Hu, Lexington, MA (US); Matthew E. Coarr, Newton, MA (US); Keith A. Crouch, Cambridge, MA (US); Hiroshi N. Fujii, Waltham, MA (US); Joshua J. Kraunelis, Lowell, MA (US); Brian P. Marx, Sharon, MA (US); Terence M. Keane, Brookline, MA (US)

(73) Assignee: The MITRE Corporation, McLean, VA (US)

( * ) Notice: Subject to any disclaimer, the term of this patent is extended or adjusted under 35 U.S.C. 154(b) by 276 days.

(21) Appl. No.: 16/889,296

(22) Filed: Jun. 1, 2020

(65) Prior Publication Data

US 2021/0369163 A1    Dec. 2, 2021

(51) Int. Cl.
*A61B 5/16* (2006.01)
*G10L 25/66* (2013.01)
(Continued)

(52) U.S. Cl.
CPC .............. *A61B 5/165* (2013.01); *A61B 5/167* (2013.01); *A61B 5/4803* (2013.01);
(Continued)

(58) Field of Classification Search
CPC ....... A61B 5/165; A61B 5/167; A61B 5/4803; A61B 5/7264; A61B 5/7275; G10L 15/02; G10L 25/63; G10L 25/66
See application file for complete search history.

(56) References Cited

U.S. PATENT DOCUMENTS 9,792,823 B2    10/2017   Zhuang et al.
10,276,188 B2    4/2019   Feast et al.
(Continued)

FOREIGN PATENT DOCUMENTS

WO    2019/081915 A1    5/2019

OTHER PUBLICATIONS

Banerjee, D. (2017) "Speech Based Machine Learning Models for Emotional State Recognition and PTSD Detection," Old Dominion University Electrical & Computer Engineering Theses & Dissertations; 147 pages.
(Continued)

*Primary Examiner* — Amanda K Hulbert
*Assistant Examiner* — Philip C Edwards
(74) *Attorney, Agent, or Firm* — Morrison & Foerster LLP

(57) ABSTRACT

Provided is a method for predicting a PTSD diagnosis in a patient comprising receiving audio input data from a patient; determining one or more audio input indicators based on the audio input data, wherein each audio input indicator of the one or more audio input indicators represents a likelihood of a positive PTSD diagnosis based on the audio input data; receiving clinical assessment data from the patient; determining one or more clinical assessment indicators based on the clinical assessment data, wherein each clinical assessment indicator of the one or more clinical assessment indicators represents a likelihood of a positive PTSD diagnosis based on the clinical assessment data; combining the one or more audio input indicators and the one or more clinical assessment indicators using a prediction model chosen by a clinician; and determining a PTSD diagnosis in the patient based on the audio input data and the clinical assessment data.

30 Claims, 8 Drawing Sheets

(51) Int. Cl.
*G10L 25/63* (2013.01)
*A61B 5/00* (2006.01)
*G10L 15/02* (2006.01)

(52) U.S. Cl.
CPC .......... *A61B 5/7264* (2013.01); *A61B 5/7275* (2013.01); *G10L 15/02* (2013.01); *G10L 25/63* (2013.01); *G10L 25/66* (2013.01)

(56) References Cited

U.S. PATENT DOCUMENTS

| | | |
|---|---|---|
| 2012/0221251 A1 | 8/2012 | Rosenberg et al. |
| 2016/0078771 A1* | 3/2016 | Zhuang .................... G09B 5/00 434/236 |
| 2017/0084295 A1 | 3/2017 | Tsiartas et al. |
| 2018/0214061 A1 | 8/2018 | Knoth et al. |

OTHER PUBLICATIONS

Garcia, P. (2012) "Objective Assessment of Post-Traumatic Stress Disorder Using Speech Analysis in Telepsychiatry," U.S. Army Medical Research and Materiel Command, Fort Detrick, Maryland 21702-5012; 10 pages.

Marmar et al. (2018) "Speech-based markers for posttraumatic stress disorder in US veterans" Anxiety and Depression Association of America; 10 pages.

* cited by examiner

SYSTEMS AND METHODS FOR HUMAN-MACHINE PARTNERED PTSD PREDICTION

STATEMENT REGARDING FEDERALLY-SPONSORED RESEARCH

This research was supported in part by the Department of Veterans Affairs including salary support and other research resources provided by the VA National Center for Post-Traumatic Stress Disorder.

FIELD OF THE DISCLOSURE

This relates to predictive systems and methods, and, more particularly, to predictive systems and methods for predicting whether individuals have post-traumatic stress disorder.

BACKGROUND OF THE DISCLOSURE

Post-traumatic stress disorder (PTSD) is a relatively common condition frequently diagnosed in individuals who have experienced severe stress and/or trauma (e.g., veterans). Symptoms of PTSD can include moderate or severe depression, intrusive dreams/nightmares, difficulty engaging in daily activities, and difficulty maintaining relationships. To ensure appropriate treatment and maximize recovery, early and accurate diagnosis is imperative.

A PTSD diagnosis is currently often based only on symptoms self-reported by a patient using either a self-report questionnaire or a clinician administered interview. During a clinical interview, the preferred method of determining diagnostic status, the clinician uses the patient's description of the symptoms and guidelines from Diagnostic and Statistical Manual of Mental Disorders (DSM-5) (https://www.psychiatry.org/psychiatrists/practice/dsm) to reach a diagnostic determination. This diagnosis is based only on information provided by the patient directly to the clinician. Thus, the diagnosis is only as accurate as the information volunteered by the patient. For example, the verbal descriptions of a patient may not be an accurate reflection of the patient's mental state. The patient can over-emphasize or under-emphasize his or her experiences in the narrative. Thus, a literal interpretation of the patient's descriptions alone, without considering other data (e.g., non-lexical cues), may lead to over-diagnosis or under-diagnosis.

In some cases, a PTSD diagnosis may be determined based on other data input. For example, speech content and vocal cues can be extracted from PTSD interview recordings. Brain imaging can reveal characteristics associated with PTSD. However, the diagnostic tools currently available to clinicians require a clinician to manually diagnose a patient using only information obtained through the patient interview.

SUMMARY OF THE DISCLOSURE

As described above, clinicians are currently required to manually diagnose a patient with PTSD using only subjective data. This means that the information a clinician uses in his or her diagnosis is only as accurate as the information provided from the patient's self-reported symptoms. Often, this subjective data source does not tell the whole story. Additionally, the diagnosis relies solely on the clinician to analyze the information provided by the single data input source to diagnose a patient. Accordingly, there is a need for a more objective, consistent, and accurate diagnostic tool for aiding a clinician in diagnosing a patient with PTSD.

Provided herein are predictive systems and methods that can help a clinician more objectively, consistently, and accurately predict whether a patient suffers from PTSD. Namely, the systems and methods provided herein include machine-and-human partnered models that are configured to receive and analyze a plurality of data input sources (e.g., speech content and vocal cues from PTSD interview recordings, patient-volunteered information, and clinician expertise). Accordingly, the predictive systems and methods provided herein can perform systematic feature extraction and predictive analysis to present the system discovered information to the doctor for the doctor's diagnostic decision-making. This can result in a more objective, consistent, comprehensive, and accurate predictive approach.

Systems and methods provided herein use algorithms to analyze the input data, but they are also configured to consider input from a clinician as well in predicting a diagnosis for a particular patient. After all, a clinician knows the patient better than a computer algorithm. Thus, system and methods provided herein accommodate some clinician discretion/input to help determine the most accurate predictive analysis to assist diagnosis for the patient.

In some embodiments, predictive systems and methods provided herein can be configured to receive and analyze a plurality of input data. For example, the plurality of input data can include speech content and/or vocal cues extracted from PTSD interview recordings, information volunteered by the patient, and/or clinician expertise. Unlike the manual predictive tools currently used by clinicians, which are only capable of analyzing one form of data source at a time, the disclosed systems and methods are configured to analyze this plurality of data input sources when determining a PTSD prediction.

Systems and methods provided herein are configured to utilize machine-learned models trained on an aggregate set of data consisting of both PTSD and non-PTSD subjects to analyze input data on a specific patient. A machine-learned model according to embodiments provided herein can compare the input data specific to an individual patient to the trained model to determine whether, based on the data, that patient likely suffers from PTSD. In some embodiments, a machine-learned model may be trained on training data that includes information about patients having a known PTSD diagnosis (i.e., a positive or negative PTSD diagnosis). For example, training data may include a plurality of interviews and/or questionnaires from people having a positive PTSD diagnosis and people having a negative PTS diagnosis. In some embodiments, the training data may be in an audio format. In some embodiments, each machine-learned model may be configured to receive and analyze a particular type of information. For example, a machine-learned model trained on audio input data may specifically look at speech emotion, vocal features, or lexical features of the audio input data to determine the likelihood of a patient's PTSD diagnosis specific to speech emotion, vocal features, or lexical features, respectively. A machine-learned model trained on clinical assessment data (e.g., questionnaire) may specifically look at social support, suicide ideation and attempts, depression severity, or self-assessment of the clinical assessment data to determine the likelihood of a patient's PTSD diagnosis specific to social support, suicide ideation and attempts, depression severity, or self-assessment, respectively.

Additionally, predictive systems and methods provided herein allow for clinician input. For example, a clinician may be able to select a specific predictive model for the system to use when analyzing the plurality of data input sources. In some embodiments, a clinician may be able to select which one or more data input source the system should analyze. The clinician may also be able to control the extent to which each data input source is weighed in relation to other data input sources of the plurality of data input sources.

BRIEF DESCRIPTION OF THE FIGURES

Various embodiments are described with reference to the accompanying figures, in which.

DETAILED DESCRIPTION OF THE DISCLOSURE

Described herein are systems and methods for objectively, accurately, and consistently predicting the likelihood of PTSD. In particular, provided are systems and methods that can receive and analyze a plurality of data input sources. The systems and methods provided can also be configured to receive and consider clinician input when predicting a PTSD diagnosis. Included also are user interfaces for clinicians to use for inputting data, adjusting the algorithm (e.g., selecting a prediction model, adjusting the weighting of each data input source), and providing a PTSD diagnosis prediction to the clinician.

Figure 1:
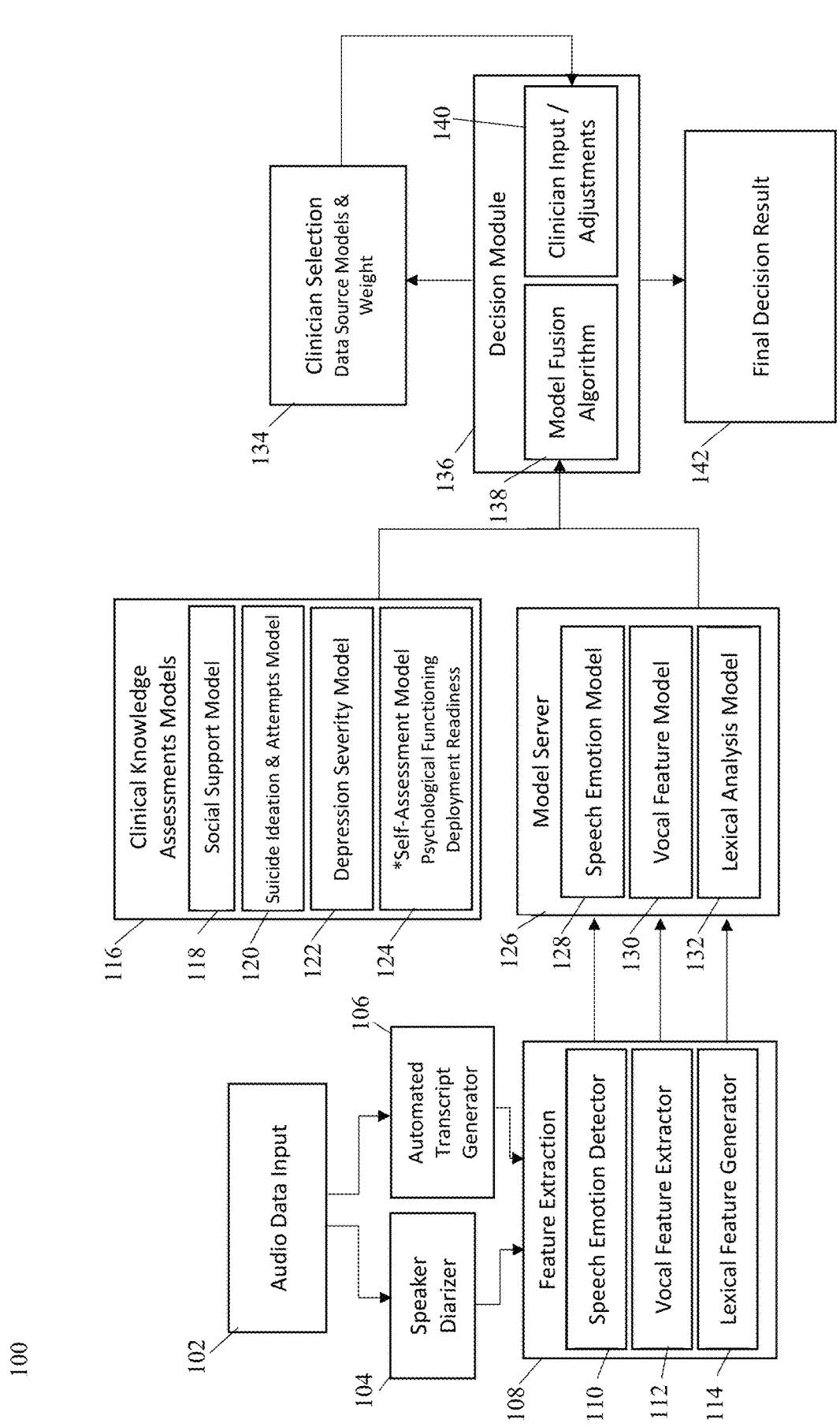
FIG. 1 depicts an exemplary process for processing a plurality of data input sources to predict a PTSD diagnosis, according to some embodiments.

FIG. 1 depicts an exemplary process for processing a plurality of data input sources to predict a PTSD diagnosis, in accordance with some embodiments. Process 100 is performed, for example, using one or more electronic devices implementing a predictive system. In some examples, process 100 is performed using a client-server system, and the blocks of process 100 are divided up in any manner between the server and a client device. In other examples, the blocks of process 100 are divided up between the server and multiple client devices. Thus, although portions of process 100 are described herein as being performed by particular devices of a client-server system, it will be appreciated that process 100 is not so limited. In other examples, process 100 is performed using only a client device or only multiple client devices. In process 100, some blocks are, optionally, combined, the order of some blocks is, optionally, changed, and some blocks are, optionally, omitted. In some examples, additional steps may be performed in combination with the process 100. Accordingly, the operations as illustrated (and described in greater detail below) are exemplary by nature and, as such, should not be viewed as limiting.

As shown in FIG. 1, a system according to embodiments herein receives, as one form of data input, audio data input 102. Audio data input 102 can include a conversation between one or more interviewers (e.g., clinicians) and one or more patients (e.g., veterans) being evaluated for PTSD. In some embodiments, the conversation captured in audio data input 102 has already taken place in the past, and the audio data input 102 includes one or more audio files. In some embodiments, the conversation captured by the audio data is ongoing, and the audio data input 102 includes a stream of audio signals sampled by one or more microphones.

Audio data input 102 can include speech from multiple speakers (e.g., clinicians, patients). The audio data input 102 can also include verbal and non-verbal information. For example, the audio data input 102 can include verbal utterances such as "I can't sleep," "I don't want to talk about it," "I don't remember," and "I have nightmares." Additionally, the audio data input 102 can include non-verbal information, such as varying speech rates and energy levels, silences, and pauses.

In some embodiments, audio data input 102 can be converted into a standard format before being further processed. The audio data input 102 can be originally stored in a first format (e.g., based on the hardware and/or software used to sample the audio data), and then converted into a second format. For example, audio data input 102 can be converted into one or more RAW files having a .pcm extension before further processing.

Once received, audio data input 102 can be diarized, or partitioned into homogeneous segments according to the speaker identity. As shown, speaker diarizer 104 is configured to analyze audio data input 102 in this manner. Speaker diarizer 104 is configured to receive information from audio data input 102, and process the information to produce a speaker diarization of the information of audio input 102.

For example, speaker diarization can be performed by speaker diarizer 104 to identify the speakers in the audio data input 102. The system can automatically identify portions of the audio data input 102 as corresponding to the patient's speech and portions of the audio data input 102 as corresponding to the clinician's speech. The segmentation can be performed using off-the-shelf algorithms, an open-source diarization SDK, or a combination thereof. Based on the segmentation, the system can determine the total amount of speech each speaker produced during the interview. Further, the segmented speech can be used to identify speech characteristics of PTSD patients and doctors (e.g., via machine learning), as discussed in detail below.

In some embodiments, speaker diarizer 104 performs automatic indexing of all words spoken by all speakers during the interview. For example, the system can associate each syllable, each word, each phrase, and/or each sentence with a speaker ID, a time stamp, and a duration value. Additional metadata (e.g., emotion, speech rate) can be associated to the words, as discussed in detail below.

In some embodiments, audio data input 102 may be automatically transcribed with automated transcript generator 106. Automated transcript generator 106 can convert the audio information of audio data input 102 into a written format using voice and speech technology. Thus, automated transcript generator 106 is configured to receive information from audio data input 102 and convert the information into a written transcript.

Once audio data input 102 is diarized and/or transcribed, the resulting speak diarization and/or transcript can be transmitted to and processed by a module configured to extract one or more types of information from the diarization and/or transcription resulting from speaker diarization 104 and automated transcription 106, respectively. Specifically, feature extraction module 108 is configured to receive one or more data input types (e.g., speaker diarization, written transcript) and determine one or more features of the information to extract.

For example, as shown in FIG. 1, feature extraction 108 can include modules such as speech emotion detector 110, vocal feature extractor 112, and/or lexical feature generator 114.

Speech emotion detector 110 can be configured to receive and analyze the input data (e.g., speaker diarization, written transcript) to detect underlying emotions. The identification of emotions can be performed by detecting audio characteristics (e.g., pitch, pitch dynamics, intensity, intensity dynamics, and spectral slope, etc.) often associated with certain types of emotional states or levels of mental vigilance. For example, when the speaker's speech rate deviates significantly from his/her normal speech rate, it indicates a change of emotional or mental state. Faster than normal speech rate can be indicative of emotions such as vigilance or excitement. In addition to speech rate, the person's vocal effort such as pitch, intonation, energy level in the speech production can also indicate the person's emotional and psychological state.

In some embodiments, emotions can be extracted from non-lexical cues such as pauses, sighs, coughs, or heavy breathing. For example, a long pause can indicate difficulty with articulation or distress. Emotions can further be extracted from filler words (e.g., "umm," "you know"). For example, a large number of filler words can indicate difficulty with articulation, hesitation, or uncertainness.

Accordingly, speech emotion detector 110 can be configured to derive these emotion features of the audio input data 102 (i.e., speaker diarization and/or transcription). This can include identifying particular features (e.g., filler words, pauses, etc.) of the input data and organizing the features according to whether they correspond to a positive PTSD diagnosis or a negative PTSD diagnosis. Once the information relating to the speech emotion of the audio input data 102 has been analyzed by speech emotion detector 110, it can be transmitted to speech emotion model 128.

Vocal feature extractor 112 can be configured to receive and analyze the input data (e.g., speaker diarization, written transcript) to detect how a speaker said the words, phrases, and sentences that he/she spoke in audio data input 102. For example, vocal feature extractor 112 can derive non-verbal cues from the audio characteristics of the recording (e.g., volume, pitches).

Vocal feature extractor 112 can include automatic detection of speech rate. In some embodiments, vocal feature extractor 112 can measure how the speech rate deviates from the normal range of an average speaker. For example, vocal feature extractor 112 can determine that a speech rate is abnormally high compared with an average speaker if the speech rate is higher than a predetermined threshold value. In addition, vocal feature extractor 112 can measure how the speech rate deviates from the speaker's average speech rate. For example, the system can determine that a speech rate is abnormally high for the speaker if the speech rate is higher than the average speech rate of the speaker during the conversation. In some embodiments, the vocal feature extractor 112 can include automatic detection of other audio characteristics such as pitch, intonation, or energy level (e.g., volume) in the speech production.

Once vocal feature extractor 112 has analyzed the input data (e.g., audio input data 102, speaker diarization and/or transcription), the analysis can be transmitted to vocal feature model 130. Specifically, vocal feature extractor 112 can be configured to derive vocal features of the input data such as pitch, energy level, speech rate, etc. These derived features can then be organized based on whether they more closely correspond to a positive PTSD diagnosis or a negative PTSD diagnosis.

Lexical feature generator 114 can be configured to receive and analyze the input data (e.g., speaker diarization, written transcript) to detect lexical features of audio input data 102. For example, lexical features can include what was said in audio data input 102. Lexical feature generator 114 can be configured to derive verbal cues from the recognized text strings.

Lexical feature generator 114 can be configured to extract PTSD-indicative words, phrases, and descriptions. In some embodiments, lexical feature generator 114 can look for the presence of one or more predefined words in the recognized text strings, such as "nightmare," "stressed," "trouble sleeping," "upset," and other pronouns. In some embodiments, lexical feature generator 114 uses one or more trained models to identify a verbal description as a PTSD indicator. For example, the system can identify sentences uttered by the patients that suggest self-harm, suicide, sleep disorders, avoidance of certain activities that are reminiscent of the traumatic experience, detachment from reality, etc. In some embodiments, the models are neural network models trained on data (e.g., previous interviews with veterans coping with PTSD) from various data sources. In some embodiments, the system uses the clinician's questions to guide the detection of PTSD indicators. For example, if the clinician asks, "Do you feel anxious," the text strings corresponding to the patient's response may be associated with the topic of "anxiety." In some embodiments, the system indexes the recognized text strings with the extracted PTSD indicators. For example, the system can associate a sentence with a tag or keyword "self-harm" or "avoidance."

In some embodiments, lexical feature generator 114 includes the extraction of patterns. For example, the system can analyze the recognized text strings to determine: words/phrases/topics frequently mentioned by the speaker, words/phrases/topics frequently emphasized by the speaker, closely associated words/phrases/topics (e.g., topics that are mentioned in proximity to each other), abrupt change of topics, etc. For example, a heavy use of pronouns rather than nouns can indicate speech impediment.

In some embodiments, lexical feature generator 114 includes type-token analysis and a summary algorithm to show the ratio of total number of unique words (type) used as compared with total number of words (frequency/token) used by a speaker. In some embodiments, lexical feature generator 114 includes analysis of how much each speaker talks in the conversation, for example, in terms of time and word count.

In some embodiments, lexical feature generator 114 includes identification of content that a speaker has failed to utter or utter properly. For example, a speaker may fail to enunciate particular words. The system can detect the speaker's failure to enunciate a word based on, for example, a low confidence score assigned to the word during the speech recognition process. As another example, the speaker may purposely avoid uttering certain words or phrases even though these words or phrases are commonly used in relation to certain scenarios (e.g., description of war). Accordingly, the system can flag the absence of these words or phrases.

Lexical feature generator 114 can be configured to derive lexical features from the input data and transmit the information to lexical analysis model 132. In particular, lexical feature generator 114 can be configured to identify lexical features from the input data (e.g., specific words, word count, etc.) and organize the features based on whether they more closely correspond to a positive PTSD diagnosis or a negative PTSD diagnosis.

The outputs of each component of feature extractor 108 (i.e., speech emotion detector 110, vocal feature extractor 112, and lexical feature generator 114) can be transmitted to model server 126. Model server 126 can include a model corresponding to each of the respective components of feature extraction 108. For example, speech emotion model 128 of model server 126 corresponds to speech emotion detector 110 and is configured to receive the output of speech emotion detector 110. Vocal feature model 130 corresponds to vocal feature extractor 112 and is configured to receive the output of vocal feature extractor 112. Additionally, lexical analysis model 132 corresponds to lexical feature generator 114 and is configured to receive the output of lexical feature generator 114.

In addition to audio data input 102, the systems and methods disclosed herein can analyze other data input sources. As shown in FIG. 1, clinical knowledge assessments 116 can include other, non-audio data input sources. For example, clinical knowledge assessments 116 can include social support 118, suicide ideation and attempts 120, depression severity 122, and self-assessment 124. These data input sources can, in some embodiments, come from clinician expertise based on interactions between the clinician and patient. For example, PTSD screening tools such as the Diagnostic and Statistical Manual of Mental Disorders, Fifth Edition (DSM-5) can be used for a clinician to help determine a patient's PTSD risk factors. In some embodiments, one or more of these non-audio data input sources (i.e., social support 118, suicide ideation and attempts 120, depression severity 122, and self-assessment 124) may be used with the systems and methods provided herein to predict whether a patient has PTSD.

Social support 118 can include information on a patient's daily life and relationships. For example, does a patient have a supportive partner or parents? Does a patient have support friends or coworkers? Does a patient surround him- or herself with other people, or does the patient frequently isolate from others? A patient who frequently isolates and/or lacks supportive relationships may be at risk for PTSD. In some embodiments, the answers to these questions may be input into a machine-learned model specific to social support. The machine-learned model can be configured to analyze the social support data and compare the data to training data. In the case of a social support machine-learned model, the training data may include a plurality of interviews (i.e., questions and answers) tagged as consistent with a positive PTSD diagnosis or a negative PTSD diagnosis. The input social support data can be compared to this training data to determine whether the input data more closely corresponds to a positive PTSD diagnosis or a negative PTSD diagnosis. Based on this analysis, social support 118 can generate an indicator. The indicator can be the output of social support 118 and can include a number from 0.0 to 1.0. For example, if this number is closer to 0.0, the patient is less likely to be lacking social support (i.e., more consistent with a negative PTSD diagnosis). As this number increases to 1.0, the patient is more likely to be lacking social support (i.e., more consistent with a positive PTSD diagnosis).

Suicide ideation and attempts 120 includes information on whether a patient is entertaining, or has entertained, thoughts of suicide. This can include actual suicidal attempts as well. Patients who entertain thoughts of suicide and/or attempt suicide may be at a greater risk of suffering from PTSD than those patients who do not. In some embodiments, the answers to these questions may be input into a machine-learned model specific to suicide ideation and attempts. The machine-learned model can be configured to analyze the suicide ideation and attempts data and compare the data to training data. In the case of a suicide ideation and attempts machine-learned model, the training data may include a plurality of interviews (i.e., questions and answers) tagged as consistent with a positive PTSD diagnosis or a negative PTSD diagnosis. The input suicide ideation and attempts data can be compared to this training data to determine whether the input data more closely corresponds to a positive PTSD diagnosis or a negative PTSD diagnosis. Based on this analysis, suicide ideation and attempts 120 can generate an indicator. The indicator can be the output of suicide ideation and attempts 120 and can include a number from 0.0 to 1.0. For example, if this number is closer to 0.0, the patient is less likely to be experiencing suicide ideations and attempts (i.e., more consistent with a negative PTSD diagnosis). As this number increases to 1.0, the patient is likely experiencing more severe suicidal ideations and/or attempts (i.e., more consistent with a positive PTSD diagnosis).

Depression severity 122 can include information on a patient's mental health as it relates to depression. For example, does the patient have mild or moderate symptoms of depression? Or is the patient severely depressed such that it greatly impacts their ability to perform basic daily tasks? Is a patient suffering from situational depression or chronic depression? Is a patient's depression symptoms triggered by external events (e.g., dreams, certain people, noises, places, etc.)? The answers to questions such as these can help a clinician gauge a patient's severity of depression. In some embodiments, the answers to these questions may be input into a machine-learned model specific to depression severity. The machine-learned model can be configured to analyze the depression severity data and compare the data to training data. In the case of a depression severity machine-learned model, the training data may include a plurality of interviews (i.e., questions and answers) tagged as consistent with a positive PTSD diagnosis or a negative PTSD diagnosis. The input depression severity data can be compared to this training data to determine whether the input data more closely corresponds to a positive PTSD diagnosis or a negative PTSD diagnosis. Based on this analysis, depression severity 120 can generate an indicator. The indicator can be the output of depression severity 120 and can include a number from 0.0 to 1.0. For example, if this number is closer to 0.0, the patient is less likely to be experiencing symptoms of depression (i.e., more consistent with a negative PTSD diagnosis). As this number increases to 1.0, the patient is likely experiencing more severe symptoms of depression (i.e., more consistent with a positive PTSD diagnosis).

Self-assessment 124 can include a patient's personal thoughts and opinions on his or her own diagnosis. Based on what he or she knows about PTSD, does he or she think that he or she suffers from the disease? This can also be useful information to have when determining whether the patient may have PTSD. In some embodiments, the answers to these questions may be input into a machine-learned model specific to a patient's self-assessment. The machine-learned model can be configured to analyze the self-assessment data and compare the data to training data. In the case of a self-assessment machine-learned model, the training data may include a plurality of interviews (i.e., questions and answers) tagged as consistent with a positive PTSD diagnosis or a negative PTSD diagnosis. The input self-assessment data can be compared to this training data to determine whether the input data more closely corresponds to a positive PTSD diagnosis or a negative PTSD diagnosis. Based on this analysis, self-assessment 124 can generate an indicator. The indicator can be the output of self-assessment 124 and can include a number from 0.0 to 1.0. For example, if this number is closer to 0.0, the patient is less likely to identify himself or herself as suffering from PTSD. As this number increases to 1.0, the patient is more likely identify himself or herself as suffering from PTSD.

The outputs (i.e., indicators) of clinical knowledge assessments 116 and model server 126 are transmitted to decision module 136. Decision module 136 is configured to receive the outputs/indicators of clinical knowledge assessments 116 and model server 126 and determine, based on this information, whether a patient may suffer from PTSD. In this analysis, decision module 136 may be configured to format the input information such that all inputs are in the same format. In some embodiments, the inputs may have already been formatted at the source (e.g., clinical knowledge assessments 116 may have determined an indicator on a scale from 0.0 to 1.0 for each data source).

For example, model fusion algorithm 138 may be configured to receive the outputs of model server 126 (e.g., speech emotion model 128, vocal feature model 130, lexical analysis model 132) and clinical knowledge assessments 116 (e.g., social support 118, suicide ideation and attempts 120, depression severity 122, self-assessment 124). Model fusion algorithm 138 can aggregate all data inputs. In some embodiments, model fusion algorithm 138 can apply default weights to each of the individual indicators received by speech emotion model 128, vocal feature model 130, lexical analysis model 132, social support 118, suicide ideation and attempts 120, depression severity 122, and self-assessment 124. In some embodiments, each of the indicators may be weighted equally. (The weights of each indicator can be modified by clinician input/adjustments 140, described below).

Based on the particular patient, a clinician may choose to adjust certain decision-making components of decision module 136 (i.e., at clinician selection 134). In some embodiments, a clinician may have the ability to adjust the weight of a particular input. For example, based on clinician expertise, information relating to a patient's social support (i.e., social support 118) may not need to be weighed as heavily in the decision algorithm as say, the patient's severity of depression (i.e., depression severity 122). In some embodiments, a clinician may adjust the data source simply because there is no data of that particular type (e.g., no audio data input 102). In some embodiments, the clinician may choose to leave out a particular data source in the PTSD analysis due to factors unique to the clinician's expertise.

In some embodiments, a clinician may have the ability to select the particular model or algorithm the system/method uses to predict whether a patient has PTSD. For example, suitable models that may be used could include an ensemble model or a heuristic model. An ensemble model uses multiple learning algorithms to obtain better predictive performance than could be obtained from any of the constituent learning algorithms alone. A heuristic model encodes decision making knowledge and/or best practices recommended by the clinician. This is in contrast to the statistical machine learning models, which derive latent characteristics from the data and use those characteristics to make a decision. A clinician might choose a heuristic model over a machine learning model because of its ability to encode knowledge/information that might not be present in the underlying data. Another reason a heuristic model may be preferred over a machine learning model is explainability, or the ability to reason about why a model made a certain decision, which can sometimes be difficult to ascertain in certain machine learning models. Other suitable predictive models that may be used can include classical regression, decision trees, neural networks, support vector machines, random forests, and/or weighted ensemble models.

As shown in FIG. 1, clinician input (i.e., clinician selection 134) is transmitted to decision module 136. Decision module 136 accounts for the multiple data source inputs (i.e., model fusion algorithm) as well as direct clinician inputs/adjustments (i.e., clinician input/adjustments 140) received from clinician selection 134.

Decision module 136 is configured to determine, based on data source inputs and clinician inputs, a prediction of whether a patient has PTSD (i.e., final decision result 142). In some embodiments, each data input source can be weighted. For example, each data input source may be weighted equally. In some embodiments, a clinician may choose to adjust the weights of each data input source based on the clinician's expertise and/or personal knowledge of the patient (i.e., using clinician selection 134).

Once decision module 136 weighs each data input source accordingly, it produces an output in the form of a prediction (i.e., final decision result 142). The prediction indicates the likelihood of whether a patient suffers from PTSD. For example, the prediction can include a probability (i.e., 0-100%) of whether the patient suffers from PTSD. In some embodiments, the prediction may include an absolute diagnostic prediction (positive or negative for PTSD) along with a confidence interval (i.e., 0-100%).

Figure 2:
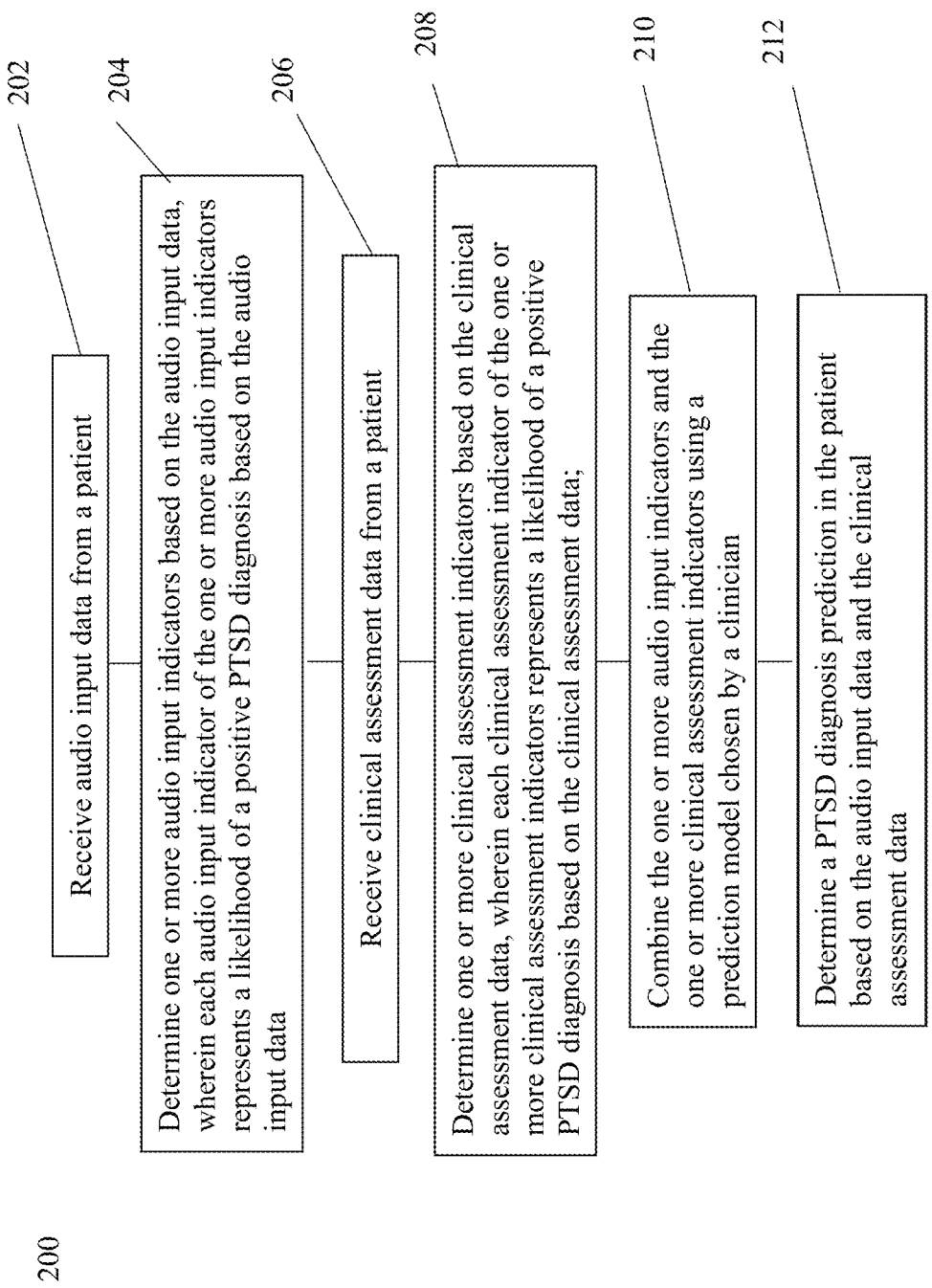
FIG. 2 depicts an exemplary process for processing a plurality of data input sources to predict a PTSD diagnosis, according to some embodiments.

FIG. 2 depicts an exemplary process for processing a plurality of data input sources to determine a PTSD prediction, in accordance with some embodiments. Process 200 is performed, for example, using one or more electronic devices implementing a predictive system. In some examples, process 200 is performed using a client-server system, and the blocks of process 200 are divided up in any manner between the server and a client device. In other examples, the blocks of process 200 are divided up between the server and multiple client devices. Thus, although portions of process 200 are described herein as being performed by particular devices of a client-server system, it will be appreciated that process 200 is not so limited. In other examples, process 200 is performed using only a client device or only multiple client devices. In process 200, some blocks are, optionally, combined, the order of some blocks is, optionally, changed, and some blocks are, optionally, omitted. In some examples, additional steps may be performed in combination with the process 100. Accordingly, the operations as illustrated (and described in greater detail below) are exemplary by nature and, as such, should not be viewed as limiting.

As shown in FIG. 2, a system receives audio input data from a patient at step 202. The audio data can be analogous to the audio data input 102 described above with reference to FIG. 1. The audio data can be part of one or more audio files and/or video files. In some embodiments, receiving audio input data includes capturing a conversation between one or more interviewers (e.g., clinicians) and one or more patients (e.g., veterans) being evaluated for PTSD.

In some embodiments, the audio input data can include metadata associated with the audio/video data. The metadata can include any information, such as information specifying the time of recording, the environment in which the recording was made (e.g., location, level of noise, setting), number of speakers, characteristics or histories of the speakers, or a combination thereof.

Once the audio input data has been received by the system at step 202, the system determines, based on the audio input data, one or more audio input indicators based on the audio input data, wherein each audio input indicator of the one or more audio input indicators represents a likelihood of a positive PTSD diagnosis based on the audio input data (i.e., at step 204). In some embodiments, determining whether a patient suffers from PTSD based on data input (e.g., audio data input from the patient) can include one or more machine-learned models. For example, step 204 may use one or more machine-learned models specific to audio data, such as a speech emotion model, a verbal features model, and/or a lexical features model. In some embodiments, each individual model has been trained on input audio data provided from patients with a known PTSD diagnosis. This training process is described in more detail with respect to FIG. 3.

Determining a likelihood of whether a patient suffers from PTSD based on the audio input data includes each machine-learned model analyzing the data and providing an indicator. Specifically, the machine-learned model determines an indicator by comparing the input data from the patient to training data associated with people having a known PTSD diagnosis (i.e., a positive PTSD diagnosis or a negative PTSD diagnosis) to determine whether the input patient data more closely corresponds to the training data consistent with a positive PTSD diagnosis or the training data consistent with a negative PTSD diagnosis. This indicator represents a patient's likelihood of suffering from PTSD based on the specific information analyzed by the model. For example, a speech emotion model analyzes the audio input data and provides, based on the audio input data and the training data used to train the speech emotion model, an indication of whether the patient suffers from PTSD (in the form of a speech emotion indicator). A vocal features model analyzes the audio input data and provides, based on the audio input data and the training data used to train the vocal features model, an indication of whether the patient suffers from PTSD (in the form of a vocal features indicator). A lexical features model analyzes the audio input data and provides, based on the audio input data and the training data used to train the vocal features model, an indication of whether the patient suffers from PTSD (in the form of a lexical features indicator). In some embodiments, each of the indicators can include a numerical value between 0 and 1.0. A number closer to 1.0 means that the specific features (e.g., speech emotion in the case of a speech emotion model) of the audio input data is more consistent with PTSD symptoms and thus, more indicative of a positive PTSD diagnosis. A number closer to 0 means that the specific features (e.g., speech emotion in the case of a speech emotion model) of the audio input data is less consistent with PTSD symptoms and thus, more indicative of a negative PTSD diagnosis.

At step 206, the system can receive clinical assessment data from the patient. Clinical assessment data can include clinical knowledge assessments 116 of FIG. 1. Clinical assessment data can include information gathered from PTSD screening assessments (e.g., Diagnostic and Statistical Manual of Mental Disorders, Fifth Edition (DSM-5)). In some embodiments, clinical assessment data can include information relating to a patient's social support, suicide ideation and attempts, depression severity, and self-assessment.

Once the clinical assessment data has been received by the system at step 206, the system determines one or more clinical assessment indicators based on the clinical assessment data, wherein each clinical assessment indicator of the one or more clinical assessment indicators represents a likelihood of a positive PTSD diagnosis based on the clinical assessment data (i.e., at step 208). In some embodiments, determining whether a patient suffers from PTSD based on data input (e.g., clinical assessment data) can include one or more machine-learned models. For example, step 208 may use one or more machine-learned models specific to clinical assessment data, such as a social support model, a suicide ideation and attempts model, a depression severity model, and/or a self-assessment model. In some embodiments, each individual model has been trained on input clinical assessment data provided from patients with a known PTSD diagnosis. This training process is described in more detail with respect to FIG. 3.

Determining a likelihood of whether a patient suffers from PTSD based on the clinical assessment data includes each machine-learned model analyzing the data and providing an indicator. Specifically, the machine-learned model determines an indicator by comparing the input data from the patient (e.g., clinical assessment data) to training data associated with people having a known PTSD diagnosis (i.e., a positive PTSD diagnosis or a negative PTSD diagnosis) to determine whether the input patient data more closely corresponds to the training data consistent with a positive PTSD diagnosis or the training data consistent with a negative PTSD diagnosis. For example, a social support model analyzes the clinical assessment data and provides, based on the clinical assessment data and the training data used to train the social support model, an indication of whether the patient suffers from PTSD (in the form of a social support indicator). A suicide ideation and attempts model analyzes the clinical assessment data and provides, based on the clinical assessment data and the training data used to train the suicide ideation and attempts model, an indication of whether the patient suffers from PTSD (in the form of a suicide ideation and attempts indicator). A depression severity model analyzes the clinical assessment data and provides, based on the clinical assessment data and the training data used to train the depression severity model, an indication of whether the patient suffers from PTSD (in the form of a depression severity indicator). A self-assessment model analyzes the clinical assessment data and provides, based on the clinical assessment data and the training data used to train the self-assessment model, an indication of whether the patient suffers from PTSD (in the form of a self-assessment indicator). In some embodiments, each of the indicators can include a numerical value between 0 and 1.0. A number closer to 1.0 means that the specific features (e.g., social support in the case of a social support model) of the clinical assessment data is more consistent with PTSD symptoms and thus, more indicative of a positive PTSD diagnosis. A number closer to 0 means that the specific features (e.g., social support in the case of a social support model) of the clinical assessment data is less consistent with PTSD symptoms and thus, more indicative of a negative PTSD diagnosis.

At step 210, the system combines the one or more audio input indicators and the one or more clinical assessment indicators. This combination can be performed by a prediction model specifically designed to consider multiple data sources (e.g., ensemble model, heuristic model). In some embodiments, a clinician may manually select which model the system uses. This selection may be based on the clinician's expertise and the patient's particular circumstances.

Once the one or more audio input indicators and the one or more clinical assessment indicators have been combined, a PTSD diagnosis of the patient can be predicted based on the audio input data and the clinical assessment data at step 212. This step can include the prediction model selected at step 210 converting the indicators (e.g., audio input data indicator and clinical assessment indicator) to a PTSD diagnosis prediction. In some embodiments, a PTSD diagnosis prediction can comprise a confidence interval.

Figure 3:
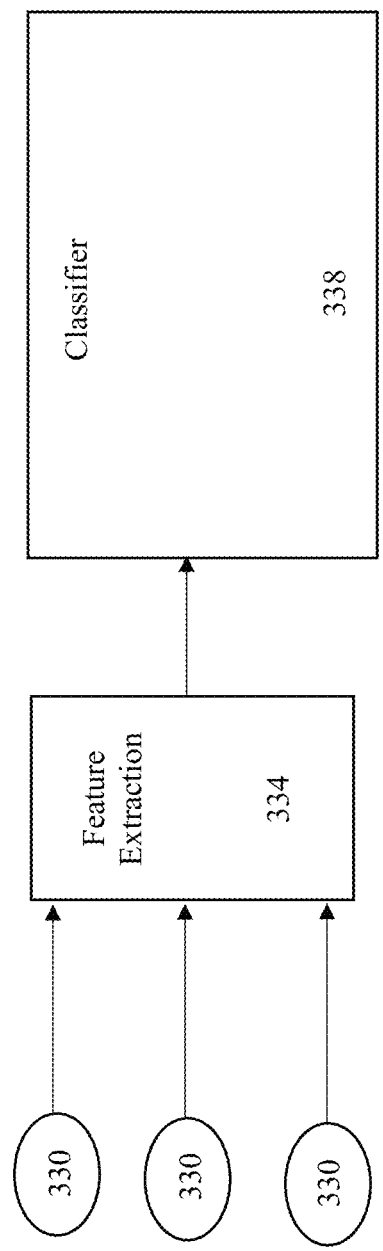
FIG. 3 depicts an exemplary process for training a machine-learned model, according to some embodiments.

FIG. 3 depicts an exemplary process 300 for training a machine-learned model that can be used to determine a PTSD diagnosis prediction, in accordance with some embodiments. Specifically, process 300 can include training data 330, feature extraction 334, and model 338.

Training data 330 can include information from patients having a known PTSD diagnosis (i.e., a positive PTSD diagnosis or a negative PTSD diagnosis). For example, training data 330 can include interviews and medical charts from people having a known PTSD diagnosis. In addition to tagging training data 330 with PTSD diagnosis, training data 330 can further be tagged or annotated according to patient's age, gender, etc. In some embodiments, training data 330 can include multiple data points from a single patient (e.g., multiple interviews). Based on training data 330, model 338 can determine patterns in training data 330 that are consistent with a positive PTSD diagnosis and patterns in training data 330 that are consistent with a negative PTSD diagnosis. For example, model 338 can utilize an algorithm that can identify, sort, and categorize the information from training data 330 to identify these patterns.

In some embodiments, algorithms may also analyze training data 330 and convert the data into a format that enables the system to identify, sort, and categorize the training data 330 information. For example, this can include extracting certain features from training data 330 (i.e., at feature extraction 334). In the case of audio input data, this may include analyzing a speech transcription and/or a speaker diarization interpretation of the audio input data to the system can analyze both verbal and non-verbal aspects of the conversation captured in the audio data input to identify indicators of PTSD. For example, common indicators of PTSD can include intrusive symptoms, avoidance of thoughts and behaviors, negative cognitions and mood, and alterations in arousal and reactivity.

In some embodiments, feature extraction 334 can include analyzing the audio input data (e.g., speaker diarization and/or speech transcription) for specific patterns in the data that may indicate a positive (or negative) PTSD diagnosis. For example, people suffering from PTSD often experience emotional fluctuations during an interview. This emotional response in a patient's voice can be measured objectively using appropriate software. To extract this data from training data 330, audio signal processing may be used to extract emotion data from the voice signal. A time-series analysis can be applied to collate the emotion data, and because the PTSD diagnosis of the particular patient associated with the input data is known, this emotion data can be tagged as consistent with, or inconsistent with, a positive PTSD diagnosis. This process may be used to develop a machine-learned model specific to speech emotion.

Feature extraction 334 may also be used to identify, sort, and categorize other forms of information from the training data. For example, feature extraction 334 may include extracting lexical information from audio training data (e.g., speaker diarization and/or speech transcription). A positive PTSD diagnosis is often associated with words/phrases indicating a recent timeframe and a patient answering "yes" to many questions posed by a clinician, and can include certain words such as "yes," "okay," "medication," "injury," "drugs," "vehicle," "remember," "memory," and "felt bad." Certain words and phrases uttered by a patient that may be indicative of a positive PTSD diagnosis in the patient can include "month," "past month," "weeks," "two weeks," "last month," health," and "emotions." On the other hand, a negative diagnosis can often be associated with distance and the patient answering "no" to most questions posed by the clinician. Terms uttered by a patient that may be indicative of a negative PTSD diagnosis can include "now," "no," "know," "nothing," and "two years." (The model may learn homophones of "no"). Certain words and phrases uttered by a patient that may be indicative of a negative PTSD diagnosis in the patient can include "two years," "last two years, "years," "last two," "past two years," "recently," and "deliberately."

To extract this data from training data 330, text strings may be identified and analyzed from the audio input data. Because the PTSD diagnosis of the particular patient associated with the input data is known, this lexical data can be tagged as consistent with, or inconsistent with, a positive PTSD diagnosis. This process may be used to develop a machine-learned model specific to lexical features.

Other machine-learned models may be trained on clinical assessment data. Clinical assessment data can include non-audio data. The non-audio data may include clinical data of a patient with or without PTSD. The specific types of clinical data that may be indicative of a positive (or negative PTSD diagnosis) can include social support, suicide ideation and attempts, depression severity, and/or self-assessment. This type of training data 330 may be in the form of a written questionnaire completed by the patient, or could be provided as clinical notes taken by the clinician. Like the feature extraction of audio data described above, feature extraction 334 of clinical assessment data can include tagging the training data 330 with a known diagnosis, gender, age, etc.

Individually-trained models for features of audio input data may include a speech emotion model, a vocal features model, and/or a lexical features model.

For example, a speech emotion model (e.g., speech emotion model 128 of FIG. 1) may be trained using training data specific to speech emotion. In some embodiments, the training data can include speech emotion features that have been extracted from audio input data (e.g., audio input data 102 of FIG. 1), as explained in detail above. The speech emotion features of the training data are tagged as being associated with a positive PTSD diagnosis or a negative PTSD diagnosis. The speech emotion model can then compare the input data to the training data to determine whether the patient corresponding to the input data exhibits speech emotion characteristics more consistent with a positive PTSD diagnosis or a negative PTSD diagnosis.

A vocal features model (e.g., vocal features model 130 of FIG. 1) may be trained using training data specific to vocal features. In some embodiments, the training data can include vocal features that have been extracted from audio input (e.g., audio input data 102 of FIG. 1), as explained in detail above. The vocal features of the training data are tagged as being associated with a positive PTSD diagnosis or a negative PTSD diagnosis. The vocal features model can then compare the input data to the training data to determine whether the patient corresponding to the input data exhibits vocal feature characteristics more consistent with a positive PTSD diagnosis or a negative PTSD diagnosis.

Additionally, a lexical features model (e.g. lexical features model 132 of FIG. 1) may be trained using training data specific to lexical features. For example, the training data can include lexical features that have been extracted from audio input (e.g., audio input 102 of FIG. 1), as explained in detail above. The lexical features of the training data are tagged as being associated with a positive PTSD diagnosis or a negative PTSD diagnosis. The lexical features model can then compare the input data to the training data to determine whether the patient corresponding to the input data exhibits lexical features more consistent with a positive PTSD diagnosis or a negative PTSD diagnosis.

Individually-trained models for features of clinical assessment data may include a social support model, a suicide ideation and attempts model, a depression severity model, and/or a self-assessment model.

In the case of a social support model (e.g., social support 118 of FIG. 1), training data specific to social support behaviors may be used. In some embodiments, training data may include questionnaires completed by individuals having a known PTSD diagnosis (i.e., either a positive diagnosis or a negative diagnosis). The social support model can identify, based on the training data, specific patterns associated with a positive PTSD diagnosis, and specific patterns associated with a negative PTSD diagnosis. The model (i.e., social support model) can compare the input data to the training data to determine whether the patient corresponding to the input data is experiencing social support behaviors more consistent with a positive PTSD diagnosis or a negative PTSD diagnosis.

In the case of a suicide ideation and attempts model (e.g., suicide ideation and attempts 120 of FIG. 1), training data specific to suicide ideation and attempt behaviors may be used. In some embodiments, training data may include questionnaires completed by individuals having a known PTSD diagnosis (i.e., either a positive diagnosis or a negative diagnosis). The suicide ideation and attempts model can identify, based on the training data, specific patterns associated with a positive PTSD diagnosis and specific patterns associated with a negative PTSD diagnosis. The model (i.e., suicide ideation and attempts model) can compare the input data to the training data to determine whether the patient corresponding to the input data is experiencing suicide ideation and attempts behaviors more consistent with a positive PTSD diagnosis or a negative PTSD diagnosis.

For a depression severity model (e.g., depression severity 122 of FIG. 1), training data specific to depression severity may be used. For example, training data may include questionnaires completed by individuals having a known PTSD diagnosis (i.e., either a positive PTSD diagnosis or a negative PTSD diagnosis). The depression severity model can identify, based on the training data, specific patterns associated with a positive PTSD diagnosis and specific patterns associated with a negative PTSD diagnosis. The model (i.e., depression severity model) can compare the input data to the training data to determine whether the patient corresponding to the input data is experiencing depression severity behaviors/symptoms more consistent with a positive PTSD diagnosis or a negative PTSD diagnosis.

For a self-assessment model (e.g., self-assessment 124 of FIG. 1), training data that includes self-assessment information may be used. For example, training data may include questionnaires completed by individuals having a known PTSD diagnosis (i.e., either a positive PTSD diagnosis or a negative PTSD diagnosis). The self-assessment model can identify, based on the training data, patterns associated with a positive PTSD diagnosis and patterns associated with a negative PTSD diagnosis. The self-assessment model can compare the input data to the training data to determine whether the patient's self-assessment input data is more consistent with a positive PTSD diagnosis or a negative PTSD diagnosis.

Figure 4:
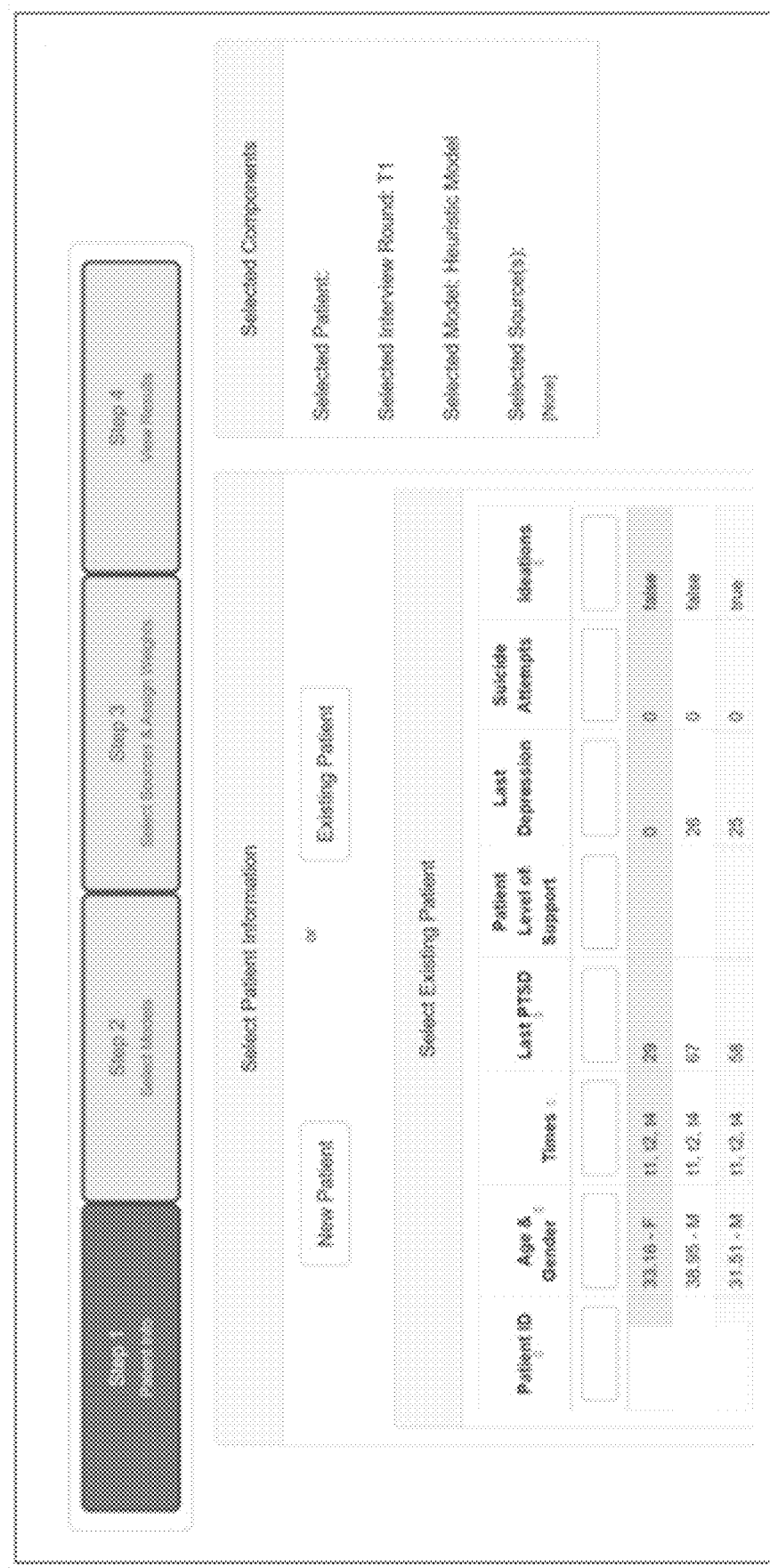
FIG. 4 depicts exemplary user interface of an electronic device, according to some embodiments.

FIG. 4 depicts a user interface of an electronic device for a clinician using the systems and methods provided herein, according to some embodiments. In particular, FIG. 4 shows a user interface display that allows a clinician to start a new PTSD prediction process (i.e., Step 1). As shown, this user interface allows a clinician to select a patient (e.g., an existing patient or a new patient). The display also includes a list of existing patients that the clinician may choose from, if he or she chooses. Each existing patient may include specific information such as age, gender, previous PTSD diagnosis, and/or previous interview data.

Figure 5:
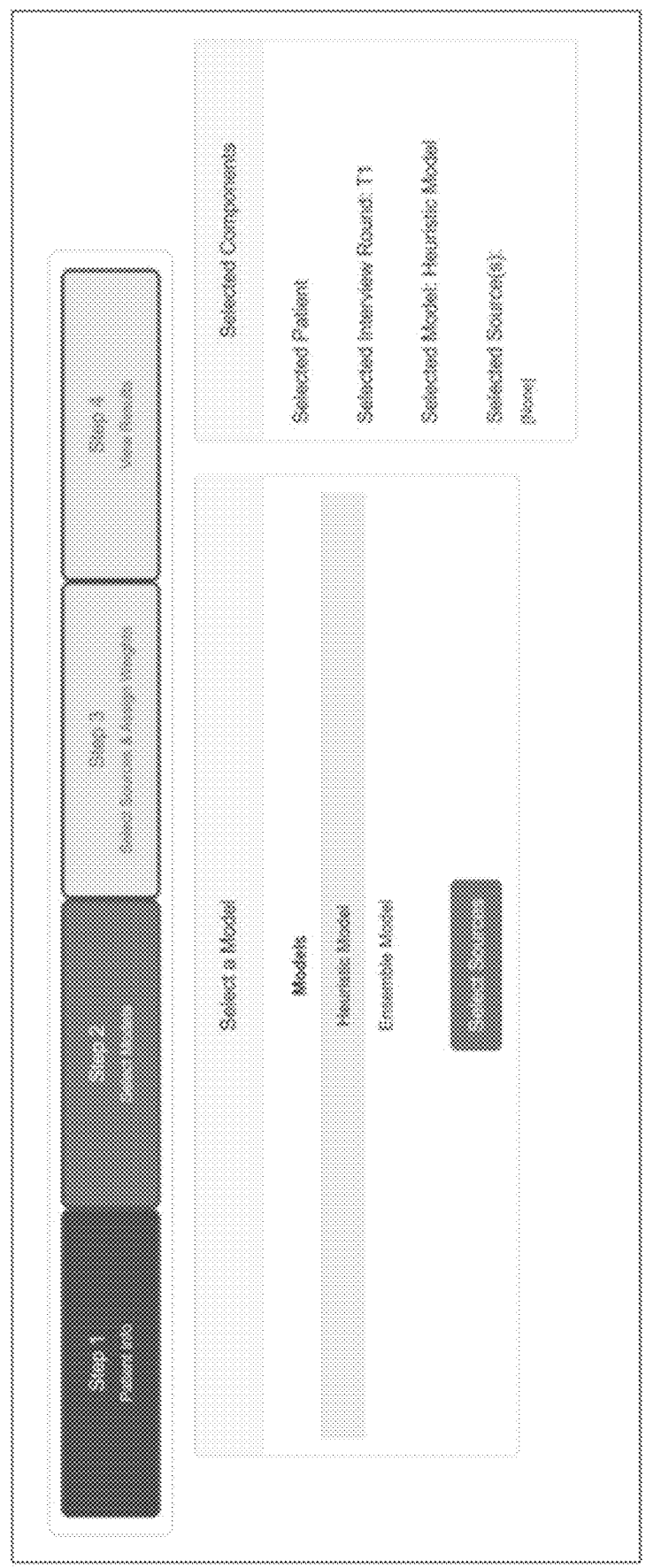
FIG. 5 depicts exemplary user interface of an electronic device, according to some embodiments.

FIG. 5 also depicts a user interface of an electronic device for a clinician using the systems and methods provided herein, according to some embodiments. Once a clinician chooses the patient in Step 1 (as described above with respect to FIG. 4), he or she may choose a prediction model in Step 2, as shown in FIG. 4. Step 2 depicted in FIG. 5 may correspond to clinician selection 134 as described above with respect to FIG. 1.

Figure 6:
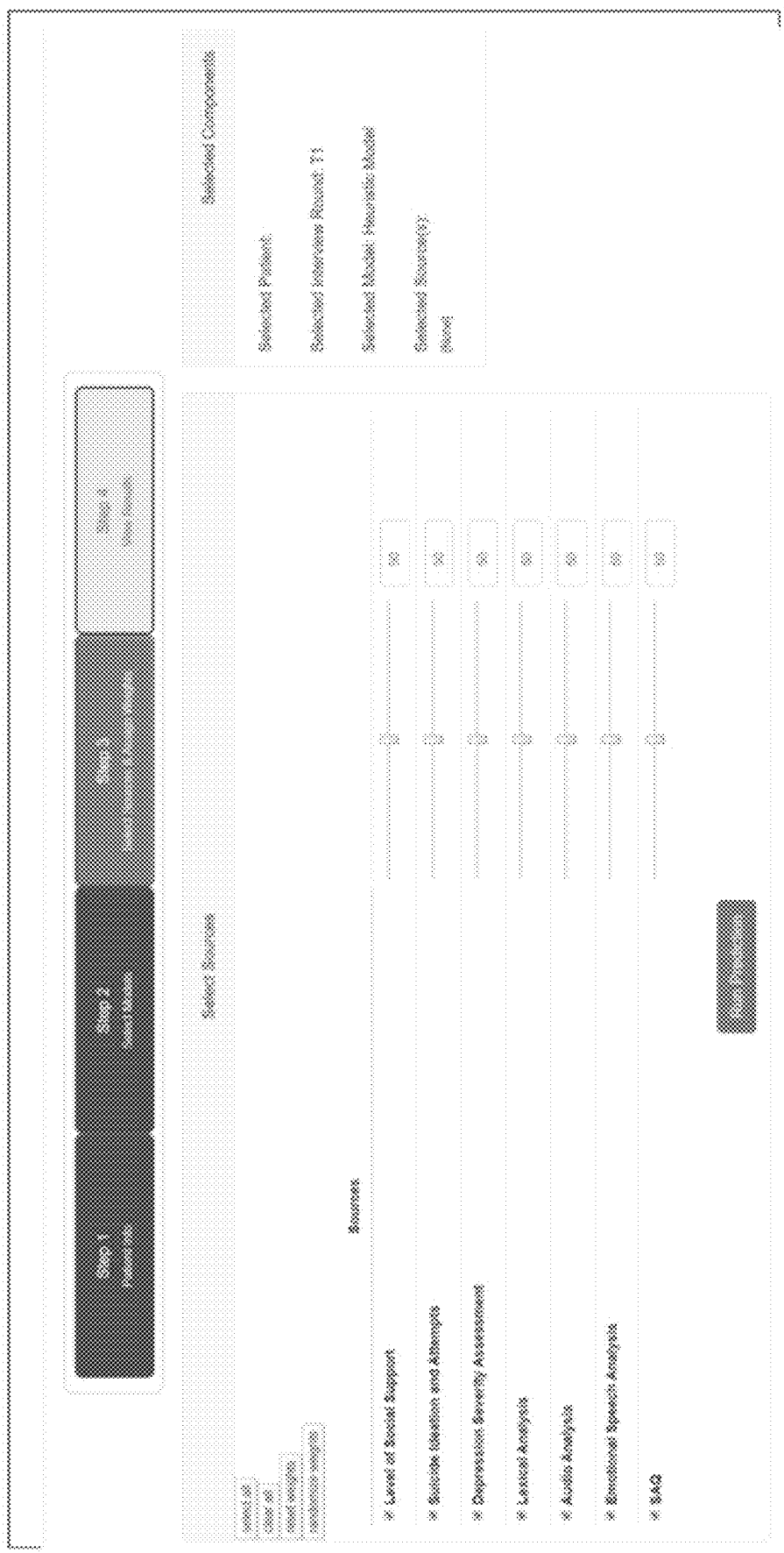
FIG. 6 depicts exemplary user interface of an electronic device, according to some embodiments.

FIG. 6 depicts a user interface of an electronic device for a clinician using the systems and methods provided herein, according to some embodiments, and in particular, FIG. 6 shows Step 3 of a PTSD prediction method. As shown, Step 3 of the method according to the user interface allows a clinician to manually adjust the weight of each of the data input sources. For example, the system may include, pre-programmed, a default weight for each data input source. In some embodiments, each data input source may be weighted equally. However, based on the data sources provided to the clinician and clinician expertise, he or she may wish to adjust the weight of each data source. This is within the discretion of the clinician, and may correspond to clinician selection 134 as described above with respect to FIG. 1. Once the clinician has adjusted the weights of each data input source as desired, he or she can select "Run Prediction."

Figure 7:
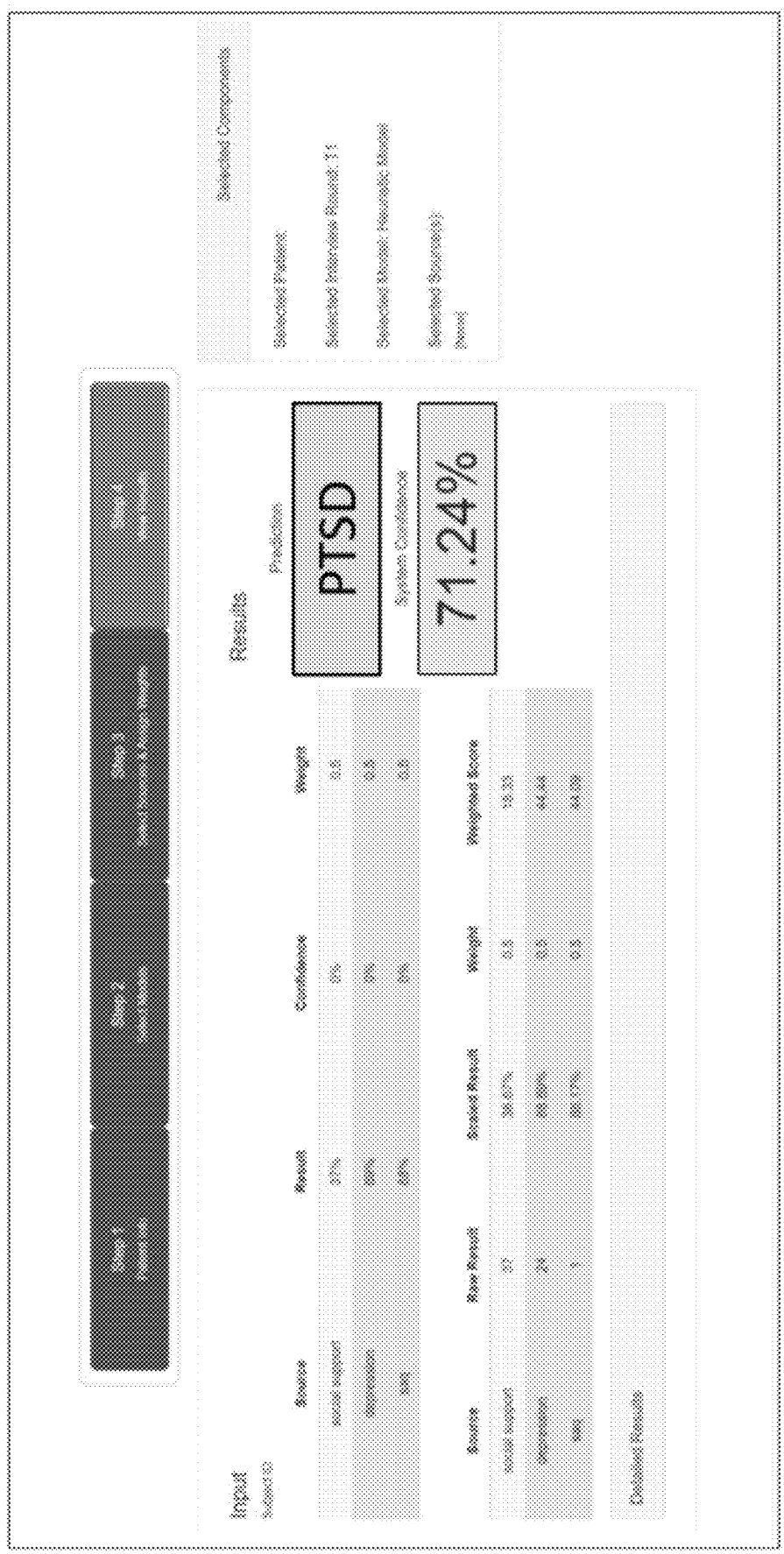
FIG. 7 depicts exemplary user interface of an electronic device, according to some embodiments.

FIG. 7 also depicts a user interface of an electronic device for a clinician using the systems and methods provided herein, according to some embodiments. In particular, FIG. 7 shows a user interface for a PTSD prediction method according to embodiments provided herein. As described above, at Step 3, a clinician selected "Run Prediction." This maneuver takes the user (i.e., clinician) to the graphic user interface shown in FIG. 7, of Step 4 of the method. Here, a clinician is provided the results of the prediction method, accounting for the particular patient that was selected, the particular prediction model that was selected, and any adjustment in weights for the specific data sources. As shown in the Figure, the system provides an indication of whether the specific patient suffers from PTSD as well as a confidence interval (e.g., 71.24%).

Figure 8:
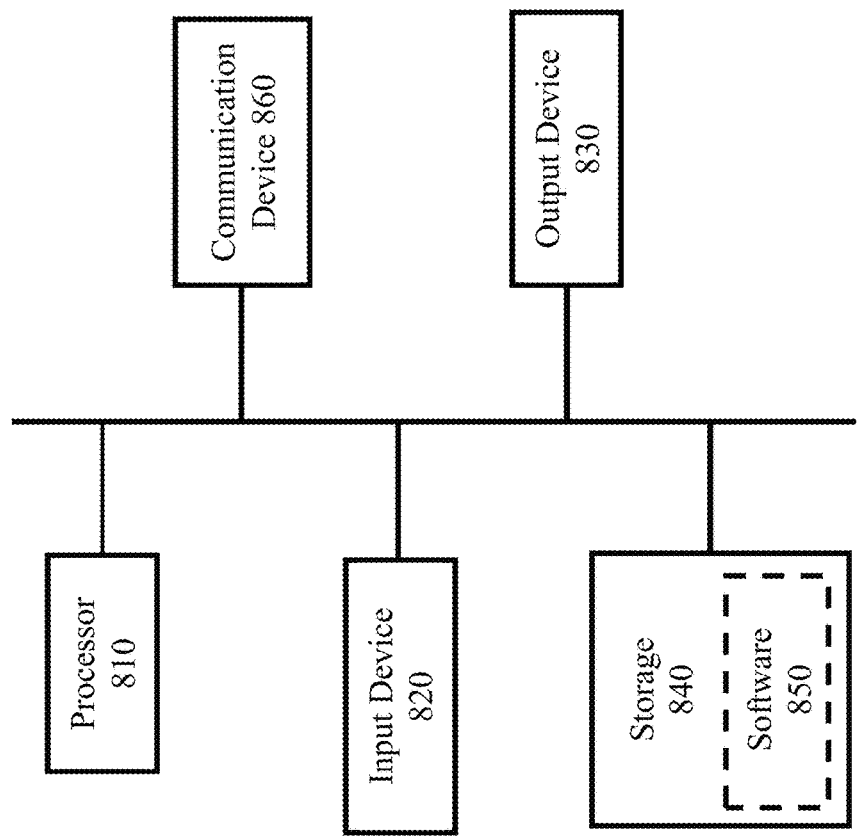
FIG. 8 illustrates a computing device, according to some embodiments.

FIG. 8 illustrates an example of a computer, according to some embodiments. Computer 800 can be a component of data investigation system according to the systems and methods described above, such as system 100 of FIG. 1, or can include the entire system itself. In some embodiments, computer 800 may execute a method for querying a data investigation system.

Computer 800 can be a host computer connected to a network. Computer 800 can be a client computer or a server. As shown in FIG. 8, computer 800 can be any suitable type of microprocessor-based device, such as a personal computer, workstation, server, or handheld computing device, such as a phone or tablet. The computer can include, for example, one or more of processor 810, input device 820, output device 830, storage 840, and communication device 860. Input device 820 and output device 830 can correspond to those described above and can either be connectable or integrated with the computer.

Input device 820 can be any suitable device that provides input, such as a touch screen or monitor, keyboard, mouse, or voice-recognition device. Output device 830 can be any suitable device that provides an output, such as a touch screen, monitor, printer, disk drive, or speaker.

Storage 840 can be any suitable device that provides storage, such as an electrical, magnetic, or optical memory, including a random access memory (RAM), cache, hard drive, CD-ROM drive, tape drive, or removable storage disk. Communication device 860 can include any suitable device capable of transmitting and receiving signals over a network, such as a network interface chip or card. The components of the computer can be connected in any suitable manner, such as via a physical bus or wirelessly. Storage 840 can be a non-transitory computer-readable storage medium comprising one or more programs, which, when executed by one or more processors, such as processor 810, cause the one or more processors to execute methods described herein.

Software 850, which can be stored in storage 840 and executed by processor 810, can include, for example, the programming that embodies the functionality of the present disclosure (e.g., as embodied in the systems, computers, servers, and/or devices as described above). In some embodiments, software 850 can include a combination of servers such as application servers and database servers.

Software 850 can also be stored and/or transported within any computer-readable storage medium for use by or in connection with an instruction execution system, apparatus, or device, such as those described above, that can fetch and execute instructions associated with the software from the instruction execution system, apparatus, or device. In the context of this disclosure, a computer-readable storage medium can be any medium, such as storage 840, that can contain or store programming for use by or in connection with an instruction execution system, apparatus, or device.

Software 850 can also be propagated within any transport medium for use by or in connection with an instruction execution system, apparatus, or device, such as those described above, that can fetch and execute instructions associated with the software from the instruction execution system, apparatus, or device. In the context of this disclosure, a transport medium can be any medium that can communicate, propagate, or transport programming for use by or in connection with an instruction execution system, apparatus, or device. The transport-readable medium can include but is not limited to, an electronic, magnetic, optical, electromagnetic, or infrared wired or wireless propagation medium.

Computer 800 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

Computer 800 can implement any operating system suitable for operating on the network. Software 850 can be written in any suitable programming language, such as C, C++, Java, or Python. In various embodiments, application software embodying the functionality of the present disclosure can be deployed in different configurations, such as in a client/server arrangement or through a Web browser as a Web-based application or Web service, for example.

Therefore, according to the above, some examples of the disclosure are directed to a method for determining a PTSD likelihood in a patient comprising: receiving audio input data from a patient; determining one or more audio input indicators based on the audio input data, wherein each audio input indicator of the one or more audio input indicators represents a likelihood of a positive PTSD diagnosis based on the audio input data; receiving clinical assessment data from the patient; determining one or more clinical assessment indicators based on the clinical assessment data, wherein each clinical assessment indicator of the one or more clinical assessment indicators represents a likelihood of a positive PTSD diagnosis based on the clinical assessment data; combining the one or more audio input indicators and the one or more clinical assessment indicators using a prediction model chosen by a clinician; and determining the PTSD diagnosis likelihood in the patient based on the audio input data and the clinical assessment data. Additionally or alternatively to one or more examples disclosed above, each audio input indicator of the one or more audio input indicators represents speech emotion, vocal features, or lexical features of the audio input data from the patient. Additionally or alternatively to one or more examples disclosed above, a first audio input indicator of the one or more audio input indicators comprises a speech emotion indicator, wherein the speech emotion indicator represents a likelihood of PTSD based on speech emotion extracted from the audio input data from the patient and compared to speech emotion training data at a machine-learned model trained on speech emotion data consistent with a positive PTSD diagnosis and speech emotion data consistent with a negative PTSD diagnosis. Additionally or alternatively to one or more examples disclosed above, a second audio input indicator of the one or more audio input indicators comprises a vocal features indicator, wherein the vocal features indicator represents a likelihood of PTSD based on vocal features extracted from the audio input data from the patient and compared to vocal features training data at a machine-learned model trained on vocal feature data consistent with a positive PTSD diagnosis and vocal feature data consistent with a negative PTSD diagnosis. Additionally or alternatively to one or more examples disclosed above, a third audio input indicator of the one or more audio input indicators comprises a lexical features indicator, wherein the lexical features indicator represents a likelihood of a positive PTSD diagnosis based on lexical features extracted from the audio input data from the patient and compared to lexical features training data at a machine-learned model trained on lexical feature data consistent with a positive PTSD diagnosis and lexical feature data consistent with a negative PTSD diagnosis. Additionally or alternatively to one or more examples disclosed above, each clinical assessment indicator of the one or more clinical assessment indicators represents social support, suicide ideation and attempts, depression severity, or self-assessment of the clinical assessment data. Additionally or alternatively to one or more examples disclosed above, a first clinical assessment indicator of the one or more clinical assessment indicators comprises a social support indicator, wherein the social support indicator represents a likelihood of a positive PTSD diagnosis based on social support features extracted from the audio input data from the patient and compared to social support training data at a machine-learned model trained on social support data consistent with a positive PTSD diagnosis and social support data consistent with a negative PTSD diagnosis. Additionally or alternatively to one or more examples disclosed above, a second clinical assessment indicator of the one or more clinical assessment indicators comprises a suicide ideation and attempts indicator, wherein the suicide ideation and attempts indicator represents a likelihood of a positive PTSD diagnosis based on suicide ideation and attempts features extracted from the audio input data from the patient and compared to suicide ideation and attempts training data at a machine-learned model trained on suicide ideation and attempts data consistent with a positive PTSD diagnosis and suicide ideation and attempts data consistent with a negative PTSD diagnosis. Additionally or alternatively to one or more examples disclosed above, a third clinical assessment indicator of the one or more clinical assessment indicators comprises a depression severity indicator, wherein the depression severity indicator represents a likelihood of a positive PTSD diagnosis based on depression severity features extracted from the audio input data from the patient and compared to depression severity training data at a machine-learned model trained on depression severity data consistent with a positive PTSD diagnosis and depression severity data consistent with a negative PTSD diagnosis. Additionally or alternatively to one or more examples disclosed above, combining the one or more audio input indicators and the one or more clinical assessment indicators comprises the clinician adjusting the weight of one or more of a speech emotion indicator, a vocal features indicator, a lexical features indicator, a social support indicator, a suicide ideation and attempts indicator, a depression severity indicator, or a self-assessment indicator.

Other examples of the disclosure are directed to a system for determining a PTSD likelihood in a patient comprising: a memory; one or more processors; and one or more programs, wherein the one or more programs are stored in the memory and configured to be executed by the one or more processors, the one or more programs when executed by the one or more processors cause the processor to: receive audio input data from a patient; determine one or more audio input indicators based on the audio input data, wherein each audio input indicator of the one or more audio input indicators represents a likelihood of a positive PTSD diagnosis based on the audio input data; receive clinical assessment data from the patient; determine one or more clinical assessment indicators based on the clinical assessment data, wherein each clinical assessment indicator of the one or more clinical assessment indicators represents a likelihood of a positive PTSD diagnosis based on the clinical assessment data; combine the one or more audio input indicators and the one or more clinical assessment indicators using a prediction model chosen by a clinician; and determine the PTSD diagnosis likelihood in the patient based on the audio input data and the clinical assessment data. Additionally or alternatively to one or more examples disclosed above, each audio input indicator of the one or more audio input indicators represents speech emotion, vocal features, or lexical features of the audio input data from the patient. Additionally or alternatively to one or more examples disclosed above, a first audio input indicator of the one or more audio input indicators comprises a speech emotion indicator, wherein the speech emotion indicator represents a likelihood of PTSD based on speech emotion extracted from the audio input data from the patient and compared to speech emotion training data at a machine-learned model trained on speech emotion data consistent with a positive PTSD diagnosis and speech emotion data consistent with a negative PTSD diagnosis. Additionally or alternatively to one or more examples disclosed above, a second audio input indicator of the one or more audio input indicators comprises a vocal features indicator, wherein the vocal features indicator represents a likelihood of PTSD based on vocal features extracted from the audio input data from the patient and compared to vocal features training data at a machine-learned model trained on vocal feature data consistent with a positive PTSD diagnosis and vocal feature data consistent with a negative PTSD diagnosis. Additionally or alternatively to one or more examples disclosed above, a third audio input indicator of the one or more audio input indicators comprises a lexical features indicator, wherein the lexical features indicator represents a likelihood of a positive PTSD diagnosis based on lexical features extracted from the audio input data from the patient and compared to lexical features training data at a machine-learned model trained on lexical feature data consistent with a positive PTSD diagnosis and lexical feature data consistent with a negative PTSD diagnosis. Additionally or alternatively to one or more examples disclosed above, each clinical assessment indicator of the one or more clinical assessment indicators represents social support, suicide ideation and attempts, depression severity, or self-assessment of the clinical assessment data. Additionally or alternatively to one or more examples disclosed above, a first clinical assessment indicator of the one or more clinical assessment indicators comprises a social support indicator, wherein the social support indicator represents a likelihood of a positive PTSD diagnosis based on social support features extracted from the audio input data from the patient and compared to social support training data at a machine-learned model trained on social support data consistent with a positive PTSD diagnosis and social support data consistent with a negative PTSD diagnosis. Additionally or alternatively to one or more examples disclosed above, a second clinical assessment indicator of the one or more clinical assessment indicators comprises a suicide ideation and attempts indicator, wherein the suicide ideation and attempts indicator represents a likelihood of a positive PTSD diagnosis based on suicide ideation and attempts features extracted from the audio input data from the patient and compared to suicide ideation and attempts training data at a machine-learned model trained on suicide ideation and attempts data consistent with a positive PTSD diagnosis and suicide ideation and attempts data consistent with a negative PTSD diagnosis. Additionally or alternatively to one or more examples disclosed above, a third clinical assessment indicator of the one or more clinical assessment indicators comprises a depression severity indicator, wherein the depression severity indicator represents a likelihood of a positive PTSD diagnosis based on depression severity features extracted from the audio input data from the patient and compared to depression severity training data at a machine-learned model trained on depression severity data consistent with a positive PTSD diagnosis and depression severity data consistent with a negative PTSD diagnosis. Additionally or alternatively to one or more examples disclosed above, combining the one or more audio input indicators and the one or more clinical assessment indicators comprises the clinician adjusting the weight of one or more of a speech emotion indicator, a vocal features indicator, a lexical features indicator, a social support indicator, a suicide ideation and attempts indicator, a depression severity indicator, or a self-assessment indicator.

Other examples of the disclosure are directed to a computer readable storage medium storing one or more programs for determining a PTSD likelihood in a patient, the one or more programs comprising instructions, which, when executed by an electronic device with a display and a user input interface, cause the device to: receive audio input data from a patient; determine one or more audio input indicators based on the audio input data, wherein each audio input indicator of the one or more audio input indicators represents a likelihood of a positive PTSD diagnosis based on the audio input data; receive clinical assessment data from the patient; determine one or more clinical assessment indicators based on the clinical assessment data, wherein each clinical assessment indicator of the one or more clinical assessment indicators represents a likelihood of a positive PTSD diagnosis based on the clinical assessment data; combine the one or more audio input indicators and the one or more clinical assessment indicators using a prediction model chosen by a clinician; and determine the PTSD diagnosis likelihood in the patient based on the audio input data and the clinical assessment data. Additionally or alternatively to one or more examples disclosed above, each audio input indicator of the one or more audio input indicators represents speech emotion, vocal features, or lexical features of the audio input data from the patient. Additionally or alternatively to one or more examples disclosed above, a first audio input indicator of the one or more audio input indicators comprises a speech emotion indicator, wherein the speech emotion indicator represents a likelihood of PTSD based on speech emotion extracted from the audio input data from the patient and compared to speech emotion training data at a machine-learned model trained on speech emotion data consistent with a positive PTSD diagnosis and speech emotion data consistent with a negative PTSD diagnosis. Additionally or alternatively to one or more examples disclosed above, a second audio input indicator of the one or more audio input indicators comprises a vocal features indicator, wherein the vocal features indicator represents a likelihood of PTSD based on vocal features extracted from the audio input data from the patient and compared to vocal features training data at a machine-learned model trained on vocal feature data consistent with a positive PTSD diagnosis and vocal feature data consistent with a negative PTSD diagnosis. Additionally or alternatively to one or more examples disclosed above, a third audio input indicator of the one or more audio input indicators comprises a lexical features indicator, wherein the lexical features indicator represents a likelihood of a positive PTSD diagnosis based on lexical features extracted from the audio input data from the patient and compared to lexical features training data at a machine-learned model trained on lexical feature data consistent with a positive PTSD diagnosis and lexical feature data consistent with a negative PTSD diagnosis. Additionally or alternatively to one or more examples disclosed above, each clinical assessment indicator of the one or more clinical assessment indicators represents social support, suicide ideation and attempts, depression severity, or self-assessment of the clinical assessment data. Additionally or alternatively to one or more examples disclosed above, a first clinical assessment indicator of the one or more clinical assessment indicators comprises a social support indicator, wherein the social support indicator represents a likelihood of a positive PTSD diagnosis based on social support features extracted from the audio input data from the patient and compared to social support training data at a machine-learned model trained on social support data consistent with a positive PTSD diagnosis and social support data consistent with a negative PTSD diagnosis. Additionally or alternatively to one or more examples disclosed above, a second clinical assessment indicator of the one or more clinical assessment indicators comprises a suicide ideation and attempts indicator, wherein the suicide ideation and attempts indicator represents a likelihood of a positive PTSD diagnosis based on suicide ideation and attempts features extracted from the audio input data from the patient and compared to suicide ideation and attempts training data at a machine-learned model trained on suicide ideation and attempts data consistent with a positive PTSD diagnosis and suicide ideation and attempts data consistent with a negative PTSD diagnosis. Additionally or alternatively to one or more examples disclosed above, a third clinical assessment indicator of the one or more clinical assessment indicators comprises a depression severity indicator, wherein the depression severity indicator represents a likelihood of a positive PTSD diagnosis based on depression severity features extracted from the audio input data from the patient and compared to depression severity training data at a machine-learned model trained on depression severity data consistent with a positive PTSD diagnosis and depression severity data consistent with a negative PTSD diagnosis. Additionally or alternatively to one or more examples disclosed above, combining the one or more audio input indicators and the one or more clinical assessment indicators comprises the clinician adjusting the weight of one or more of a speech emotion indicator, a vocal features indicator, a lexical features indicator, a social support indicator, a suicide ideation and attempts indicator, a depression severity indicator, or a self-assessment indicator.

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

As used herein, the singular forms "a," "an," and "the" are intended to include the plural forms as well, unless the context clearly indicates otherwise. It is also to be understood that the term "and/or" as used herein refers to and encompasses any and all possible combinations of one or more of the associated listed items. It is further to be understood that the terms "includes, "including," "comprises," and/or "comprising," when used herein, specify the presence of stated features, integers, steps, operations, elements, components, and/or units but do not preclude the presence or addition of one or more other features, integers, steps, operations, elements, components, units, and/or groups thereof.

This application discloses several numerical ranges in the text and figures. The numerical ranges disclosed inherently support any range or value within the disclosed numerical ranges, including the endpoints, even though a precise range limitation is not stated verbatim in the specification because this disclosure can be practiced throughout the disclosed numerical ranges.

The foregoing description, for the purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims.

The invention claimed is:

1. A method for determining a PTSD likelihood in a patient comprising:
receiving, at an electronic device, audio input data from a patient;
determining one or more audio input indicators based on the audio input data, wherein each audio input indicator of the one or more audio input indicators represents a likelihood of a positive PTSD diagnosis based on the audio input data;
receiving, at the electronic device, clinical assessment data from the patient, wherein the clinical assessment data comprises one or more of social support data, suicide ideation and attempts data, depression severity data, or self-assessment data;
determining one or more clinical assessment indicators based on the clinical assessment data, wherein each clinical assessment indicator of the one or more clinical assessment indicators represents a likelihood of a positive PTSD diagnosis based on the clinical assessment data;
combining, at a decision module of the electronic device, the one or more audio input indicators and the one or more clinical assessment indicators using a heuristic model; and
determining, by the heuristic model at the decision module of the electronic device, the PTSD diagnosis likelihood in the patient based on the audio input data and the clinical assessment data.

2. The method of claim 1, wherein each audio input indicator of the one or more audio input indicators represents speech emotion, vocal features, or lexical features of the audio input data from the patient.

3. The method of claim 2, wherein a first audio input indicator of the one or more audio input indicators comprises a speech emotion indicator, wherein the speech emotion indicator represents a likelihood of PTSD based on speech emotion extracted from the audio input data from the patient and compared to speech emotion training data at a machine-learned model trained on speech emotion data consistent with a positive PTSD diagnosis and speech emotion data consistent with a negative PTSD diagnosis.

4. The method of claim 2, wherein a second audio input indicator of the one or more audio input indicators comprises a vocal features indicator, wherein the vocal features indicator represents a likelihood of PTSD based on vocal features extracted from the audio input data from the patient and compared to vocal features training data at a machine-learned model trained on vocal feature data consistent with a positive PTSD diagnosis and vocal feature data consistent with a negative PTSD diagnosis.

5. The method of 2, wherein a third audio input indicator of the one or more audio input indicators comprises a lexical features indicator, wherein the lexical features indicator represents a likelihood of a positive PTSD diagnosis based on lexical features extracted from the audio input data from the patient and compared to lexical features training data at a machine-learned model trained on lexical feature data consistent with a positive PTSD diagnosis and lexical feature data consistent with a negative PTSD diagnosis.

6. The method of claim 1, wherein each clinical assessment indicator of the one or more clinical assessment indicators represents social support, suicide ideation and attempts, depression severity, or self-assessment of the clinical assessment data.

7. The method of claim 6, wherein a first clinical assessment indicator of the one or more clinical assessment indicators comprises a social support indicator, wherein the social support indicator represents a likelihood of a positive PTSD diagnosis based on social support features extracted from the audio input data from the patient and compared to social support training data at a machine-learned model trained on social support data consistent with a positive PTSD diagnosis and social support data consistent with a negative PTSD diagnosis.

8. The method of claim 6, wherein a second clinical assessment indicator of the one or more clinical assessment indicators comprises a suicide ideation and attempts indicator, wherein the suicide ideation and attempts indicator represents a likelihood of a positive PTSD diagnosis based on suicide ideation and attempts features extracted from the audio input data from the patient and compared to suicide ideation and attempts training data at a machine-learned model trained on suicide ideation and attempts data consistent with a positive PTSD diagnosis and suicide ideation and attempts data consistent with a negative PTSD diagnosis.

9. The method of claim 6, wherein a third clinical assessment indicator of the one or more clinical assessment indicators comprises a depression severity indicator, wherein the depression severity indicator represents a likelihood of a positive PTSD diagnosis based on depression severity features extracted from the audio input data from the patient and compared to depression severity training data at a machine-learned model trained on depression severity data consistent with a positive PTSD diagnosis and depression severity data consistent with a negative PTSD diagnosis.

10. The method of claim 1, wherein combining the one or more audio input indicators and the one or more clinical assessment indicators comprises the clinician adjusting the weight of one or more of a speech emotion indicator, a vocal features indicator, a lexical features indicator, a social support indicator, a suicide ideation and attempts indicator, a depression severity indicator, or a self-assessment indicator.

11. A system for determining a PTSD likelihood in a patient comprising:
a memory;
one or more processors; and
one or more programs, wherein the one or more programs are stored in the memory and configured to be executed by the one or more processors, the one or more programs when executed by the one or more processors cause the processor to:

receive audio input data from a patient at an electronic device;

determine one or more audio input indicators based on the audio input data, wherein each audio input indicator of the one or more audio input indicators represents a likelihood of a positive PTSD diagnosis based on the audio input data;

receive clinical assessment data from the patient at the electronic device, wherein the clinical assessment data comprises one or more of social support data, suicide ideation and attempts data, depression severity data, or self-assessment data;

determine one or more clinical assessment indicators based on the clinical assessment data, wherein each clinical assessment indicator of the one or more clinical assessment indicators represents a likelihood of a positive PTSD diagnosis based on the clinical assessment data;

combine the one or more audio input indicators and the one or more clinical assessment indicators using a heuristic model at a decision module of the electronic device; and determine by the heuristic model the PTSD diagnosis likelihood in the patient based on the audio input data and the clinical assessment data at the decision module of the electronic device.

12. The system of claim 11, wherein each audio input indicator of the one or more audio input indicators represents speech emotion, vocal features, or lexical features of the audio input data from the patient.

13. The system of claim 12, wherein a first audio input indicator of the one or more audio input indicators comprises a speech emotion indicator, wherein the speech emotion indicator represents a likelihood of PTSD based on speech emotion extracted from the audio input data from the patient and compared to speech emotion training data at a machine-learned model trained on speech emotion data consistent with a positive PTSD diagnosis and speech emotion data consistent with a negative PTSD diagnosis.

14. The system of claim 12, wherein a second audio input indicator of the one or more audio input indicators comprises a vocal features indicator, wherein the vocal features indicator represents a likelihood of PTSD based on vocal features extracted from the audio input data from the patient and compared to vocal features training data at a machine-learned model trained on vocal feature data consistent with a positive PTSD diagnosis and vocal feature data consistent with a negative PTSD diagnosis.

15. The system of 12, wherein a third audio input indicator of the one or more audio input indicators comprises a lexical features indicator, wherein the lexical features indicator represents a likelihood of a positive PTSD diagnosis based on lexical features extracted from the audio input data from the patient and compared to lexical features training data at a machine-learned model trained on lexical feature data consistent with a positive PTSD diagnosis and lexical feature data consistent with a negative PTSD diagnosis.

16. The system of claim 11, wherein each clinical assessment indicator of the one or more clinical assessment indicators represents social support, suicide ideation and attempts, depression severity, or self-assessment of the clinical assessment data.

17. The system of claim 16, wherein a first clinical assessment indicator of the one or more clinical assessment indicators comprises a social support indicator, wherein the social support indicator represents a likelihood of a positive PTSD diagnosis based on social support features extracted from the audio input data from the patient and compared to social support training data at a machine-learned model trained on social support data consistent with a positive PTSD diagnosis and social support data consistent with a negative PTSD diagnosis.

18. The system of claim 16, wherein a second clinical assessment indicator of the one or more clinical assessment indicators comprises a suicide ideation and attempts indicator, wherein the suicide ideation and attempts indicator represents a likelihood of a positive PTSD diagnosis based on suicide ideation and attempts features extracted from the audio input data from the patient and compared to suicide ideation and attempts training data at a machine-learned model trained on suicide ideation and attempts data consistent with a positive PTSD diagnosis and suicide ideation and attempts data consistent with a negative PTSD diagnosis.

19. The system of claim 16, wherein a third clinical assessment indicator of the one or more clinical assessment indicators comprises a depression severity indicator, wherein the depression severity indicator represents a likelihood of a positive PTSD diagnosis based on depression severity features extracted from the audio input data from the patient and compared to depression severity training data at a machine-learned model trained on depression severity data consistent with a positive PTSD diagnosis and depression severity data consistent with a negative PTSD diagnosis.

20. The system of claim 11, wherein combining the one or more audio input indicators and the one or more clinical assessment indicators comprises the clinician adjusting the weight of one or more of a speech emotion indicator, a vocal features indicator, a lexical features indicator, a social support indicator, a suicide ideation and attempts indicator, a depression severity indicator, or a self-assessment indicator.

21. A computer readable storage medium storing one or more programs for determining a PTSD likelihood in a patient, the one or more programs comprising instructions, which, when executed by an electronic device with a display and a user input interface, cause the device to:

receive audio input data from a patient at an electronic device;

determine one or more audio input indicators based on the audio input data, wherein each audio input indicator of the one or more audio input indicators represents a likelihood of a positive PTSD diagnosis based on the audio input data;

receive clinical assessment data from the patient at the electronic device, wherein the clinical assessment data comprises one or more of social support data, suicide ideation and attempts data, depression severity data, or self-assessment data;

determine one or more clinical assessment indicators based on the clinical assessment data, wherein each clinical assessment indicator of the one or more clinical assessment indicators represents a likelihood of a positive PTSD diagnosis based on the clinical assessment data;

combine the one or more audio input indicators and the one or more clinical assessment indicators using a heuristic model at a decision module of the electronic device; and determine by the heuristic model the PTSD diagnosis likelihood in the patient based on the audio input data and the clinical assessment data at the decision module of the electronic device.

22. The computer readable storage medium of claim 21, wherein each audio input indicator of the one or more audio input indicators represents speech emotion, vocal features, or lexical features of the audio input data from the patient.

23. The computer readable storage medium of claim 22, wherein a first audio input indicator of the one or more audio input indicators comprises a speech emotion indicator, wherein the speech emotion indicator represents a likelihood of PTSD based on speech emotion extracted from the audio input data from the patient and compared to speech emotion training data at a machine-learned model trained on speech emotion data consistent with a positive PTSD diagnosis and speech emotion data consistent with a negative PTSD diagnosis.

24. The computer readable storage medium of claim 22, wherein a second audio input indicator of the one or more audio input indicators comprises a vocal features indicator, wherein the vocal features indicator represents a likelihood of PTSD based on vocal features extracted from the audio input data from the patient and compared to vocal features training data at a machine-learned model trained on vocal feature data consistent with a positive PTSD diagnosis and vocal feature data consistent with a negative PTSD diagnosis.

25. The computer readable storage medium of 22, wherein a third audio input indicator of the one or more audio input indicators comprises a lexical features indicator, wherein the lexical features indicator represents a likelihood of a positive PTSD diagnosis based on lexical features extracted from the audio input data from the patient and compared to lexical features training data at a machine-learned model trained on lexical feature data consistent with a positive PTSD diagnosis and lexical feature data consistent with a negative PTSD diagnosis.

26. The computer readable storage medium of claim 21, wherein each clinical assessment indicator of the one or more clinical assessment indicators represents social support, suicide ideation and attempts, depression severity, or self-assessment of the clinical assessment data.

27. The computer readable storage medium of claim 26, wherein a first clinical assessment indicator of the one or more clinical assessment indicators comprises a social support indicator, wherein the social support indicator represents a likelihood of a positive PTSD diagnosis based on social support features extracted from the audio input data from the patient and compared to social support training data at a machine-learned model trained on social support data consistent with a positive PTSD diagnosis and social support data consistent with a negative PTSD diagnosis.

28. The computer readable storage medium of claim 26, wherein a second clinical assessment indicator of the one or more clinical assessment indicators comprises a suicide ideation and attempts indicator, wherein the suicide ideation and attempts indicator represents a likelihood of a positive PTSD diagnosis based on suicide ideation and attempts features extracted from the audio input data from the patient and compared to suicide ideation and attempts training data at a machine-learned model trained on suicide ideation and attempts data consistent with a positive PTSD diagnosis and suicide ideation and attempts data consistent with a negative PTSD diagnosis.

29. The computer readable storage medium of claim 26, wherein a third clinical assessment indicator of the one or more clinical assessment indicators comprises a depression severity indicator, wherein the depression severity indicator represents a likelihood of a positive PTSD diagnosis based on depression severity features extracted from the audio input data from the patient and compared to depression severity training data at a machine-learned model trained on depression severity data consistent with a positive PTSD diagnosis and depression severity data consistent with a negative PTSD diagnosis.

30. The computer readable storage medium of claim 21, wherein combining the one or more audio input indicators and the one or more clinical assessment indicators comprises the clinician adjusting the weight of one or more of a speech emotion indicator, a vocal features indicator, a lexical features indicator, a social support indicator, a suicide ideation and attempts indicator, a depression severity indicator, or a self-assessment indicator.

* * * * *